(12) United States Patent
Aranyi et al.

(10) Patent No.: US 10,111,665 B2
(45) Date of Patent: Oct. 30, 2018

(54) ELECTROMECHANICAL SURGICAL SYSTEMS

(71) Applicant: Covidien LP, Mansfield, MA (US)

(72) Inventors: Ernest Aranyi, Easton, CT (US); Kenneth H. Whitfield, North Haven, CT (US); David Farascioni, Bethel, CT (US)

(73) Assignee: Covidien LP, Mansfield, MA (US)

( * ) Notice: Subject to any disclaimer, the term of this patent is extended or adjusted under 35 U.S.C. 154(b) by 407 days.

(21) Appl. No.: 14/886,297

(22) Filed: Oct. 19, 2015

(65) Prior Publication Data

US 2016/0242779 A1    Aug. 25, 2016

Related U.S. Application Data

(60) Provisional application No. 62/118,239, filed on Feb. 19, 2015.

(51) Int. Cl.
*A61B 17/04* (2006.01)
*A61B 17/10* (2006.01)
(Continued)

(52) U.S. Cl.
CPC .......... *A61B 17/105* (2013.01); *A61B 17/068* (2013.01); *A61B 17/07207* (2013.01);
(Continued)

(58) Field of Classification Search
CPC .............. A61B 17/068; A61B 17/1155; A61B 2017/00477; A61B 17/105
(Continued)

(56) References Cited

U.S. PATENT DOCUMENTS 2,777,340 A    1/1957  Hettwer et al.
2,957,353 A    10/1960 Babacz
(Continued)

FOREIGN PATENT DOCUMENTS

CA    2451558 A1    1/2003
CA    2824590 A1    4/2014
(Continued)

OTHER PUBLICATIONS

European Search Report for EP16156250.9 date of completion is Sep. 15, 2016 (5 pages).
(Continued)

*Primary Examiner* — Robert Long

(57) ABSTRACT

An electromechanical surgical system includes an electromechanical surgical device, an adapter assembly, and a surgical loading unit. The adapter assembly includes a rotatable drive sleeve configured to receive a rotatable drive connector of the surgical device, a single rotatable drive shaft rotatably connected to the drive sleeve, and a gear disposed around a distal end of the drive shaft. The loading unit includes a cartridge jaw including a mounting portion defining a receiving channel, a power screw disposed within the receiving channel, a gear member mounted on a proximal portion of the power screw and operably engagable with the gear of the adapter assembly, and a locking mechanism disposed within the mounting portion for locking the loading unit to the adapter assembly that is movable between an unlocked position when the cartridge jaw is free of a cartridge and a locked position when a cartridge is loaded therein.

7 Claims, 7 Drawing Sheets

(51) Int. Cl.
*A61B 17/072* (2006.01)
*A61B 17/068* (2006.01)
A61B 17/00 (2006.01)
A61B 17/29 (2006.01)
A61B 90/00 (2016.01)

(52) U.S. Cl.
CPC ............... A61B 2017/0046 (2013.01); A61B 2017/00398 (2013.01); A61B 2017/00473 (2013.01); A61B 2017/00477 (2013.01); A61B 2017/00734 (2013.01); A61B 2017/07214 (2013.01); A61B 2017/07271 (2013.01); A61B 2017/2932 (2013.01); A61B 2090/0808 (2016.02)

(58) Field of Classification Search
USPC ........................................... 227/175.1–182.1
See application file for complete search history.

(56) References Cited

U.S. PATENT DOCUMENTS

| | | | |
|---|---|---|---|
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,874,181 A | 10/1989 | Hsu | |
| 5,033,552 A * | 7/1991 | Hu ..................... | B25B 21/00 173/170 |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,427,087 A | 6/1995 | Ito et al. | |
| 5,433,721 A | 7/1995 | Hooven et al. | |
| 5,467,911 A | 11/1995 | Tsuruta et al. | |
| 5,476,379 A | 12/1995 | Disel | |
| 5,486,185 A * | 1/1996 | Freitas ............... | A61B 17/2909 606/142 |
| 5,487,499 A | 1/1996 | Sorrentino et al. | |
| 5,507,772 A * | 4/1996 | Shutt .................. | A61B 17/1608 606/205 |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,626,587 A | 5/1997 | Bishop et al. | |
| 5,632,432 A | 5/1997 | Schulze et al. | |
| 5,645,209 A | 7/1997 | Green et al. | |
| 5,647,526 A | 7/1997 | Green et al. | |
| 5,653,374 A | 8/1997 | Young et al. | |
| 5,658,300 A | 8/1997 | Bito et al. | |
| 5,662,662 A | 9/1997 | Bishop et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,792,573 A | 8/1998 | Pitzen et al. | |
| 5,797,536 A | 8/1998 | Smith et al. | |
| 5,820,009 A | 10/1998 | Melling et al. | |
| 5,863,159 A | 1/1999 | Lasko | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,860,892 B1 | 3/2005 | Tanaka et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 7,032,798 B2 | 4/2006 | Whitman et al. | |
| RE39,152 E | 6/2006 | Aust et al. | |
| 7,055,731 B2 | 6/2006 | Shelton, IV et al. | |
| 7,059,508 B2 | 6/2006 | Shelton, IV et al. | |
| 7,077,856 B2 | 7/2006 | Whitman | |
| 7,111,769 B2 | 9/2006 | Wales et al. | |
| 7,122,029 B2 | 10/2006 | Koop et al. | |
| 7,140,528 B2 | 11/2006 | Shelton, IV | |

(56) References Cited

U.S. PATENT DOCUMENTS

| | | |
|---|---|---|
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |

(56) References Cited

U.S. PATENT DOCUMENTS

| | | |
|---|---|---|
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,402,604 B2* | 8/2016 | Williams ......... A61B 17/07207 |
| 9,797,486 B2* | 10/2017 | Zergiebel ................ F16H 19/02 |
| 9,801,646 B2* | 10/2017 | Zergiebel ....... A61B 17/320016 |
| 9,826,976 B2* | 11/2017 | Parihar ............... A61B 17/068 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0032179 A1* | 2/2010 | Hanspers ................ B25F 3/00 173/11 |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0181322 A1 | 7/2012 | Whitman et al. |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0200131 A1* | 8/2013 | Racenet ............... A61B 17/072 227/180.1 |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0005677 A1 | 1/2014 | Shelton, IV et al. |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0110456 A1* | 4/2014 | Taylor ................. A61B 17/072 227/176.1 |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0305989 A1* | 10/2014 | Parihar ............. A61B 17/0686 227/176.1 |
| 2014/0305992 A1* | 10/2014 | Kimsey ................ A61B 17/068 227/176.1 |
| 2014/0332243 A1* | 11/2014 | Baskar ...................... B25F 5/02 173/29 |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |

(56) References Cited

U.S. PATENT DOCUMENTS

| | | | |
|---|---|---|---|
| 2015/0112381 A1 | 4/2015 | Richard | |
| 2015/0122870 A1 | 5/2015 | Zemlok et al. | |
| 2015/0133224 A1 | 5/2015 | Whitman et al. | |
| 2015/0133957 A1 | 5/2015 | Kostrzewski | |
| 2015/0150547 A1 | 6/2015 | Ingmanson et al. | |
| 2015/0150574 A1 | 6/2015 | Richard et al. | |
| 2015/0157320 A1 | 6/2015 | Zergiebel et al. | |
| 2015/0157321 A1 | 6/2015 | Zergiebel et al. | |
| 2015/0164502 A1 | 6/2015 | Richard et al. | |
| 2015/0201931 A1 | 7/2015 | Zergiebel et al. | |
| 2015/0272577 A1 | 10/2015 | Zemlok et al. | |
| 2015/0297199 A1 | 10/2015 | Nicholas et al. | |
| 2015/0303996 A1 | 10/2015 | Calderoni | |
| 2015/0320420 A1 | 11/2015 | Penna et al. | |
| 2015/0327850 A1 | 11/2015 | Kostrzewski | |
| 2015/0342601 A1 | 12/2015 | Williams et al. | |
| 2015/0342603 A1 | 12/2015 | Zergiebel et al. | |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0095585 A1 | 4/2016 | Zergiebel et al. | |
| 2016/0095596 A1 | 4/2016 | Scirica et al. | |
| 2016/0100839 A1* | 4/2016 | Marczyk | A61B 17/07207 227/175.3 |
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |
| 2016/0157856 A1* | 6/2016 | Williams | A61B 17/068 227/175.1 |
| 2016/0192934 A1* | 7/2016 | Williams | A61B 17/105 227/176.1 |
| 2016/0192938 A1* | 7/2016 | Sgroi, Jr. | A61B 17/1155 227/175.1 |
| 2016/0249909 A1* | 9/2016 | Shelton, IV | A61B 17/068 227/176.1 |
| 2016/0310134 A1* | 10/2016 | Contini | A61B 17/07207 |
| 2016/0324518 A1* | 11/2016 | Nicholas | A61B 17/068 |
| 2017/0079660 A1* | 3/2017 | Sgroi | A61B 17/068 |

FOREIGN PATENT DOCUMENTS

| | | |
|---|---|---|
| CN | 102247182 A | 11/2011 |
| DE | 102008053842 A1 | 5/2010 |
| EP | 0705571 A1 | 4/1996 |
| EP | 1769754 A1 | 4/2007 |
| EP | 2055243 A2 | 5/2009 |
| EP | 2316345 A1 | 5/2011 |
| EP | 2333509 A1 | 6/2011 |
| EP | 2668910 A2 | 12/2013 |
| EP | 2764833 A2 | 8/2014 |
| EP | 2777528 A2 | 9/2014 |
| EP | 2777530 A1 | 9/2014 |
| ES | 2333509 A1 | 2/2010 |
| JP | 08-038488 | 2/1996 |
| JP | 2005-125075 A | 5/2005 |
| KR | 20120022521 A | 3/2012 |
| WO | 2011/108840 A2 | 9/2011 |
| WO | 2012/040984 A1 | 4/2012 |

OTHER PUBLICATIONS

Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian 2016 Examination Report No. 1 corresponding to International Application No. AU 2014204542 dated Jan. 7, 2016.
Chinese Office Action corresponding to International Application No. CN 201310125449.6 dated Feb. 3, 2016.
Extended 2016 European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended 24, 2015 European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended 2015 European Search Report corresponding to International Application No. EP 14 19 7563.1 dated Aug. 5, 2015.
Partial European Search Report corresponding to International Application No. EP 15 19 0643.5 dated Feb. 26, 2016.
Extended 2016 European Search Report corresponding to International Application No. EP 15 16 6899.3 dated Feb. 3, 2016.
Extended 22, 2015 European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.

* cited by examiner

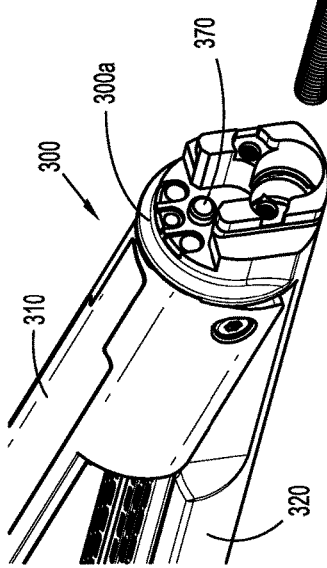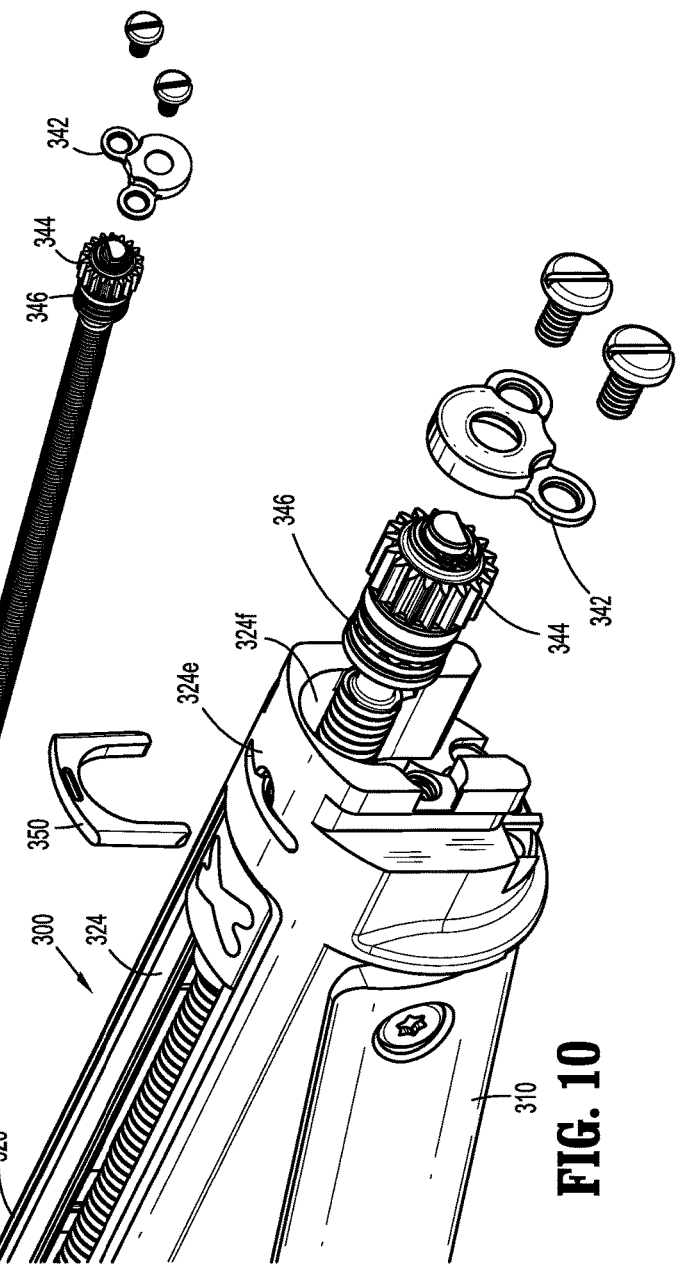

ELECTROMECHANICAL SURGICAL SYSTEMS

CROSS-REFERENCE TO RELATED APPLICATIONS

This application claims the benefit of and priority to U.S. Provisional Patent Application No. 62/118,239, filed Feb. 19, 2015, the entire disclosure of which is incorporated by reference herein.

TECHNICAL FIELD

The present disclosure relates to electromechanical surgical systems. More specifically, the present disclosure relates to adapter assemblies having a single rotational drive shaft to electrically and mechanically interconnect an end effector that is configured to perform a function and a surgical device that is configured to actuate the end effector, and end effectors having a locking mechanism for attachment to an adapter assembly.

BACKGROUND

A number of surgical device manufacturers have developed product lines with proprietary powered drive systems for operating and/or manipulating a surgical device. In many instances the surgical devices include a powered handle assembly, which is reusable, and a disposable end effector or the like that is selectively connected to the powered handle assembly prior to use and then disconnected from the powered handle assembly following use in order to be disposed of or in some instances sterilized for re-use.

Many of the existing end effectors for use with many of the existing powered surgical devices and/or handle assemblies are driven by a linear force. For example, end effectors for performing endo-gastrointestinal anastomosis procedures, end-to-end anastomosis procedures, and transverse anastomosis procedures, each typically require a linear driving force in order to be operated. As such, these end effectors are not compatible with surgical devices and/or handle assemblies that use a rotary motion to deliver power or the like.

In order to make the linear driven end effectors compatible with powered surgical devices and/or handle assemblies that use a rotary motion to deliver power, adapters and/or adapter assemblies are used to interface between and interconnect the linear driven end effectors with the powered rotary driven surgical devices and/or handle assemblies. Many of these adapter and/or adapter assemblies are complex devices including many parts that require extensive labor to assemble. Accordingly, a need exists to develop adapters and/or adapter assemblies that incorporate fewer parts, are less labor intensive to assemble, and are ultimately more economical to manufacture. In addition, a need exists for locking mechanisms which ensure proper coupling of an adapter/adapter assembly to an end effector.

SUMMARY

According to an aspect of the present disclosure, an electromechanical surgical system includes a handheld electromechanical surgical device, an adapter assembly, and a surgical loading unit. The surgical device includes at least one rotatable drive connector supported in a handle housing and the adapter assembly includes at least one rotatable drive sleeve configured to receive the at least one rotatable drive connector. The adapter assembly also includes a single rotatable drive shaft rotatably connected to the at least one rotatable drive sleeve that longitudinally extends to a distal end of the adapter assembly. A gear is disposed around a distal end of the rotatable drive shaft and configured to rotate with the rotatable drive shaft. The surgical loading unit includes an anvil jaw and a cartridge jaw that are joined to one another such that the anvil jaw and the cartridge jaw are movable between open and closed positions relative to one another. The cartridge jaw includes a mounting portion defining a receiving channel, a power screw disposed within the receiving channel of the mounting portion, a gear member mounted on a proximal portion of the power screw and operably engagable with the gear of the adapter assembly, and a locking mechanism disposed within the mounting portion for locking the surgical loading unit to the adapter assembly. The locking mechanism is movable between an unlocked position when the cartridge jaw is free of a cartridge and a locked position when a cartridge is loaded into the cartridge jaw. The locking mechanism may be biased to the unlocked position by a spring.

The locking mechanism may include a frame that is axially movable within a proximal portion of the mounting portion when the cartridge is loaded into and unloaded from the cartridge jaw. In embodiments, the frame includes a rod longitudinally extending proximally therefrom and dimensioned to extend through an opening in a proximal end of the mounting portion. The rod extends proximally through the opening in the proximal end of the mounting portion when in the locked position and is recessed within or distal to the opening when in the unlocked position. In some embodiments, the rod extends into a recess in the distal end of the adapter assembly when in the locked position.

In some embodiments, the anvil jaw and the cartridge jaw are pinned together by a pair of pins extending through axially opposed openings in sidewalls of each of the anvil jaw and the cartridge jaw, and the frame includes a pair of transverse slots extending parallel to a longitudinal axis of the frame that are aligned with the opposed openings in the sidewall of the cartridge jaw such that the pins extend through the opposed openings and into the slots. The slots have a larger axial dimension than the openings in the sidewall such that when the locking mechanism is in the locked position the pins are disposed within a distal portion of the slots and when the locking mechanism is in the unlocked position the pins are disposed in a proximal portion of the slots.

The electromechanical surgical system may include a lock member positioned through the sidewall of the mounting portion and into a distal bearing member to axially lock the power screw within the cartridge jaw.

According to another aspect of the present disclosure, a surgical loading unit that is selectively interconnectable with an adapter assembly including a rotatable drive shaft, includes an anvil jaw and a cartridge jaw including a mounting portion defining a receiving channel therein. A fastener firing assembly is disposed within the mounting portion and includes a power screw and a gear member disposed at a proximal end of the power screw that is operably engagable with the rotatable drive shaft of the adapter assembly. A cartridge including a plurality of fasteners therein is removably loadable into the receiving channel of the mounting portion. A locking mechanism is disposed within the mounting portion for locking the surgical loading unit to the adapter assembly. The locking mechanism is operably associated with the cartridge such that loading the cartridge into the mounting portion moves the locking mechanism into a locked position and unloading the cartridge from the mounting portion moves the locking mechanism into an unlocked position. The locking mechanism may be biased to the unlocked position by a spring.

The locking mechanism may include a frame that is axially movable within a proximal portion of the mounting portion when the cartridge is loaded into and unloaded from the cartridge jaw. In embodiments, the frame includes a rod longitudinally extending proximally therefrom that is dimensioned to extend through an opening in a proximal end of the mounting portion. The rod extends proximally through the opening in the proximal end of the mounting portion when in the locked position and is recessed within or distal to the opening when in the unlocked position.

In some embodiments, the frame includes a pair of transverse slots extending parallel to a longitudinal axis of the frame and aligned with opposed openings in a sidewall of the cartridge jaw that are dimensioned to receive pins for interconnecting the cartridge jaw with the anvil jaw. The slots have a larger axial dimension than the openings in the sidewall such that when the locking mechanism is in the locked position the pins are disposed within a distal portion of the slots and when the locking mechanism is in the unlocked position the pins are disposed in a proximal portion of the slots.

The surgical loading unit may include a lock member positioned through a sidewall of the mounting portion and into a distal bearing member of the fastener firing assembly to axially lock the power screw within the cartridge jaw.

According to another aspect of the present disclosure, a method of securing a surgical loading unit to an adapter assembly includes: positioning a surgical loading unit, that is free of a cartridge, and an adapter assembly along parallel longitudinal axes such that mating surfaces on a proximal end of the surgical loading unit and on a distal end of the adapter assembly are aligned along a transverse axis; sliding at least one of the surgical loading unit and the adapter assembly along the transverse axis to join the mating surfaces and align the surgical loading unit and the adapter assembly along a common axis; and loading a cartridge within a cartridge jaw of the surgical loading unit to move a locking mechanism of the cartridge jaw from a biased, unlocked position in which a rod of the locking mechanism does not extend proximal of the mating surface of the surgical loading unit to a locked position in which the rod extends proximal of the mating surface of the surgical loading unit and into a recess defined within the distal end of the adapter assembly to lock the surgical loading unit to the adapter assembly.

In embodiments, the locking mechanism includes a camming surface at a distal end thereof, such that loading the cartridge includes longitudinally pushing the camming surface proximally thereby moving the locking mechanism towards the adapter assembly. The method may include unloading the cartridge to unlock the surgical loading unit from the adapter assembly.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 9 is an enlarged top perspective view of the surgical loading unit of FIGS. 1 and 6-8 with a portion of a fastener firing assembly shown separated from a cartridge jaw of the surgical loading unit;

FIG. 10 is an enlarged side perspective view of the surgical loading unit of FIGS. 1 and 6-9 with a lock member and a portion of a fastener firing assembly shown separated from a cartridge jaw of the surgical loading unit;

DETAILED DESCRIPTION

Figure 1:
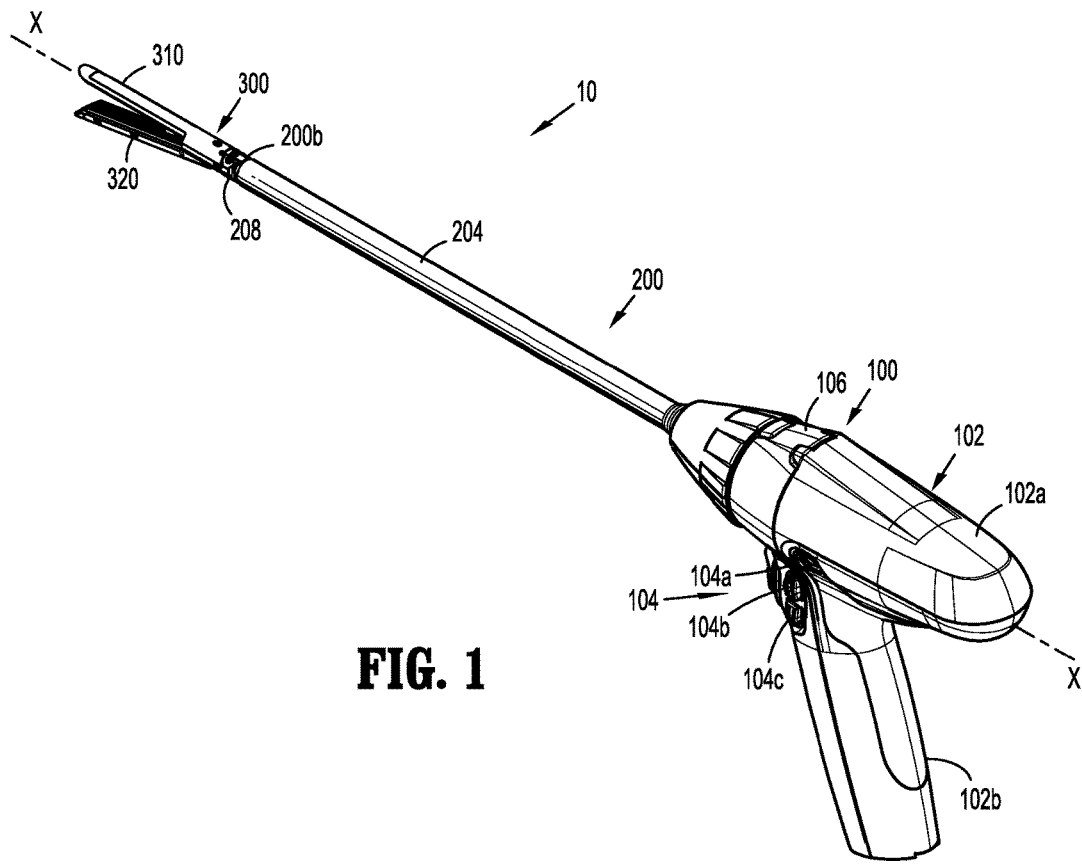
FIG. 1 is a perspective view of an electromechanical surgical system in accordance with the principles of the present disclosure.

Electromechanical surgical systems of the present disclosure include surgical devices in the form of powered handheld electromechanical instruments configured for selective attachment to a plurality of different end effectors that are each configured for actuation and manipulation by the powered handheld electromechanical surgical instrument. In particular, the presently described electromechanical surgical systems include adapter assemblies that interconnect the powered handheld electromechanical surgical instruments to a plurality of different end effectors.

Embodiments of the presently disclosed electromechanical surgical systems, surgical devices/handle assemblies, adapter assemblies, and/or end effectors are described in detail with reference to the drawings, in which like reference numerals designate identical or corresponding elements in each of the several views. As used herein the term "distal" refers to a portion of a structure that is farther from a user, while the term "proximal" refers to a portion of a structure that is closer to a user.

Figure 2:
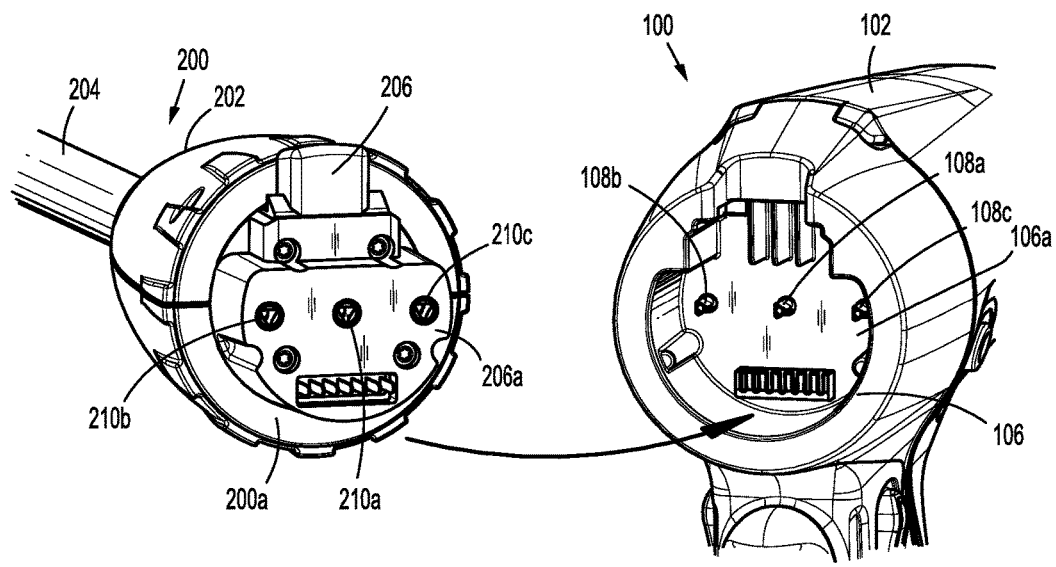
FIG. 2 is a perspective view illustrating an attachment of a proximal end of an adapter assembly to a distal end of a surgical device of FIG. 1.

Turning now to FIGS. 1 and 2, an electromechanical surgical system, in accordance with the present disclosure, generally referred to as 10, includes a surgical device 100 in the form of a powered handheld electromechanical instrument, an adapter assembly 200, and an end effector, such as a surgical loading unit 300 (e.g., multiple- or single-use loading units). For the purposes of discussion, the end effectors will be discussed in terms of surgical loading units; however, the disclosed electromechanical surgical assemblies can be used with a variety of end effectors within the purview of those skilled in the art, such as, for example, clamping jaws and cutting tools. Surgical device 100 is configured for selective connection with adapter assembly 200, and, in turn, adapter assembly 200 is configured for selective connection with surgical loading unit 300. Together, surgical device 100 and adapter assembly 200 may cooperate to actuate surgical loading unit 300.

Surgical device 100 includes a handle housing 102 including an upper housing portion 102a and a lower housing portion 102b. Upper housing portion 102a houses various components of surgical device 100 therein, such as a circuit board (not shown) that is configured to control various operations of surgical device 100 and a drive mechanism (not shown) that is configured to drive shafts and/or gear components in order to perform various operations of surgical device 100. In particular, the drive mechanism may be configured to drive shafts and/or gear components in order to selectively articulate surgical loading unit 300 about a longitudinal axis "X" and relative to a distal end of adapter assembly 200, to selectively rotate loading unit 300 about longitudinal axis "X" and relative to handle housing 102, to selectively move/approximate/separate an anvil jaw 310 and a cartridge receiving jaw (hereinafter, cartridge jaw) 320 of surgical loading unit 300 relative to one another, and/or to fire a stapling and cutting cartridge (not shown) disposed within cartridge jaw 320 of surgical loading unit 300. The lower housing portion 102b supports a trigger housing 104 including a plurality of finger-actuated control buttons, rocker devices, and the like 104a, 104b, and 104c for activating the various functions performed by the drive mechanism. Lower housing portion 102b also defines a cavity therein for selective removable receipt of a power source, such as a rechargeable battery (not shown), which is electrically interconnected with electrical components situated in the upper housing portion 102a.

Upper housing portion 102a of handle housing 102 defines a connecting portion 106 at a distal end thereof that is configured to accept a proximal end of adapter assembly 200. Connecting portion 106 has a cylindrical recess 106a that houses a plurality of rotatable drive connectors 108a, 108b, and 108c arranged in a common plane or line with one another. As can be appreciated, the plurality of rotatable drive connectors can be arranged in any suitable configuration. Each rotatable drive connector 108a, 108b, and 108c can be independently, and/or dependently, actuatable and rotatable by the drive mechanism (not shown) housed within handle housing 102. The drive mechanism may be configured to selectively drive one or more of rotatable drive connectors 108a, 108b, and 108c of surgical device 100, at a given time.

For a detailed description of various internal components and operation of exemplary electromechanical surgical systems, the components of which are combinable and/or interchangeable with one or more components of electromechanical surgical systems 10 described herein, reference may be made to International Application No. PCT/US2008/077249, filed Sep. 22, 2008 (Inter. Pub. No. WO 2009/039506), U.S. Patent Application Publication No. 2011/0121049, filed on Nov. 20, 2009, and U.S. Patent Application Publication No. 2012/0253329 filed on May 31, 2012, the entire contents of each of which are incorporated herein by reference.

Figure 3:
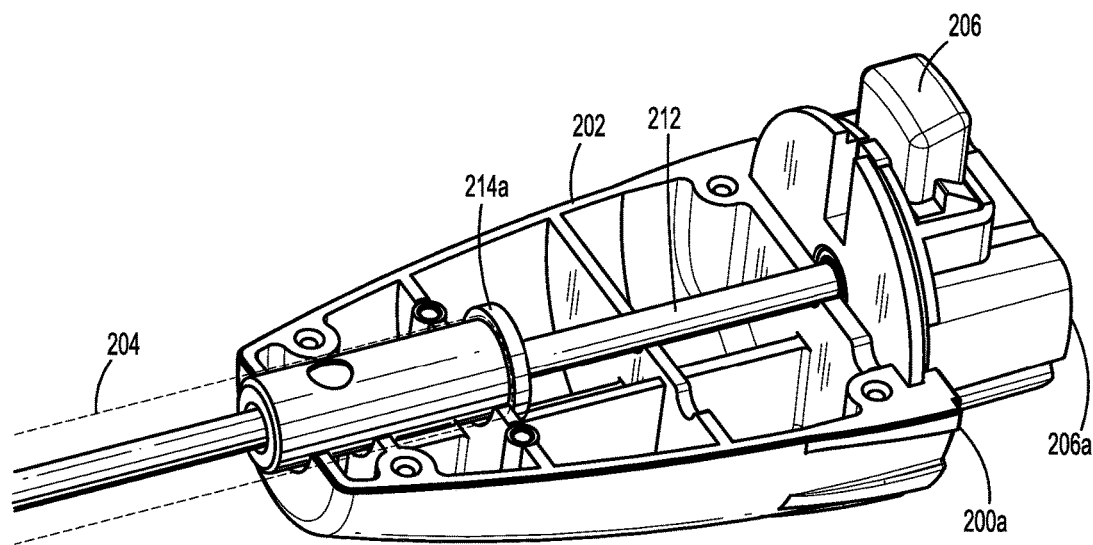
FIG. 3 is a top perspective view of the adapter assembly of FIGS. 1 and 2 with a top half portion of an adapter housing removed.
Figure 4:
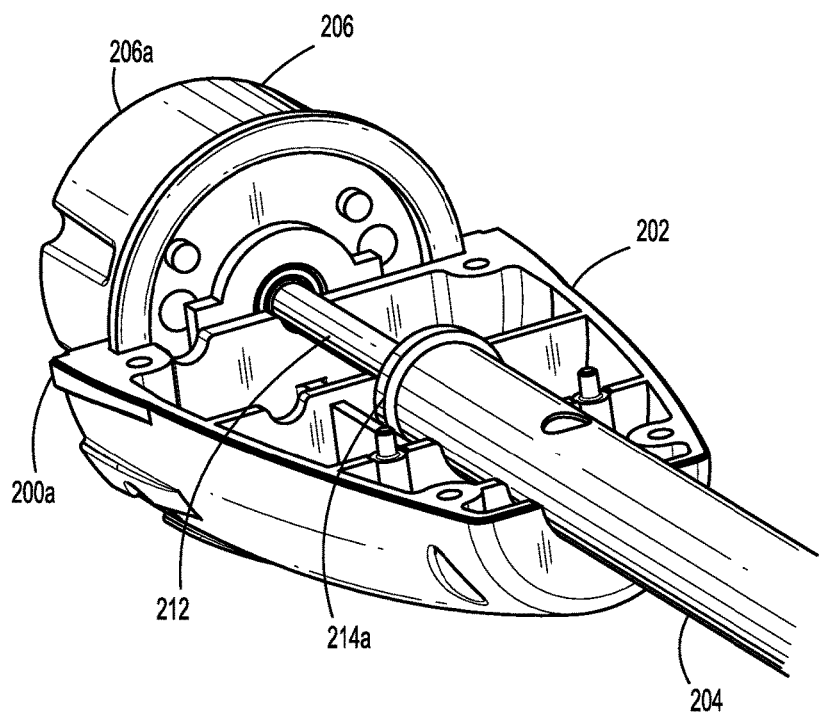
FIG. 4 is a bottom perspective view of the adapter assembly of FIGS. 1-3 with a bottom half portion of the adapter housing removed.
Figure 5:
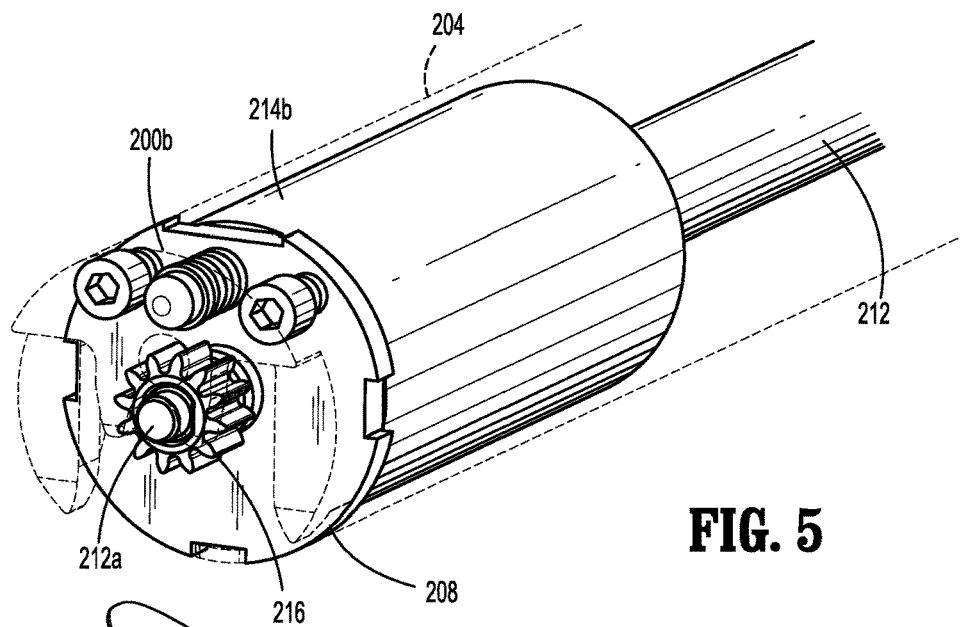
FIG. 5 is a perspective view of a distal end of the adapter assembly of FIGS. 1-4 with an outer tube shown in phantom.
Figure 6:
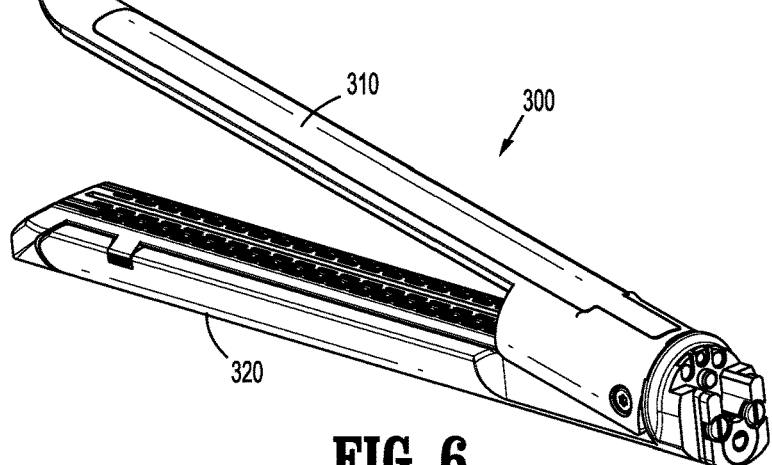
FIG. 6 is a top perspective view of a surgical loading unit of FIG. 1.
Figure 7:
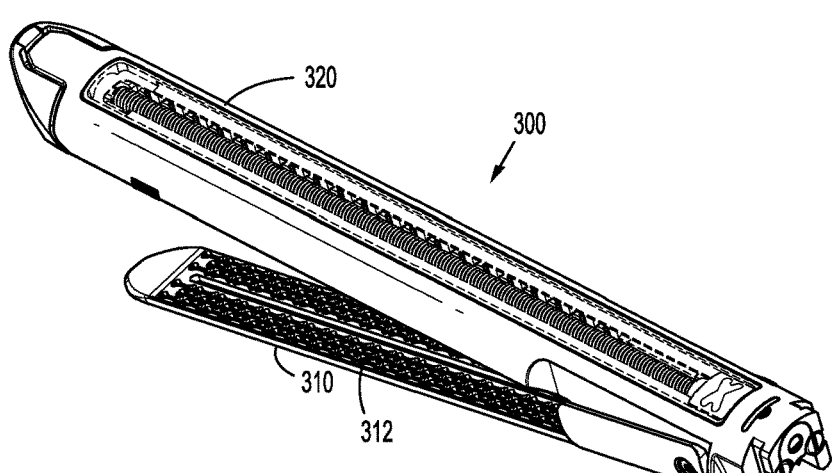
FIG. 7 is a bottom perspective view of the surgical loading unit of FIGS. 1 and 6.
Figure 8:
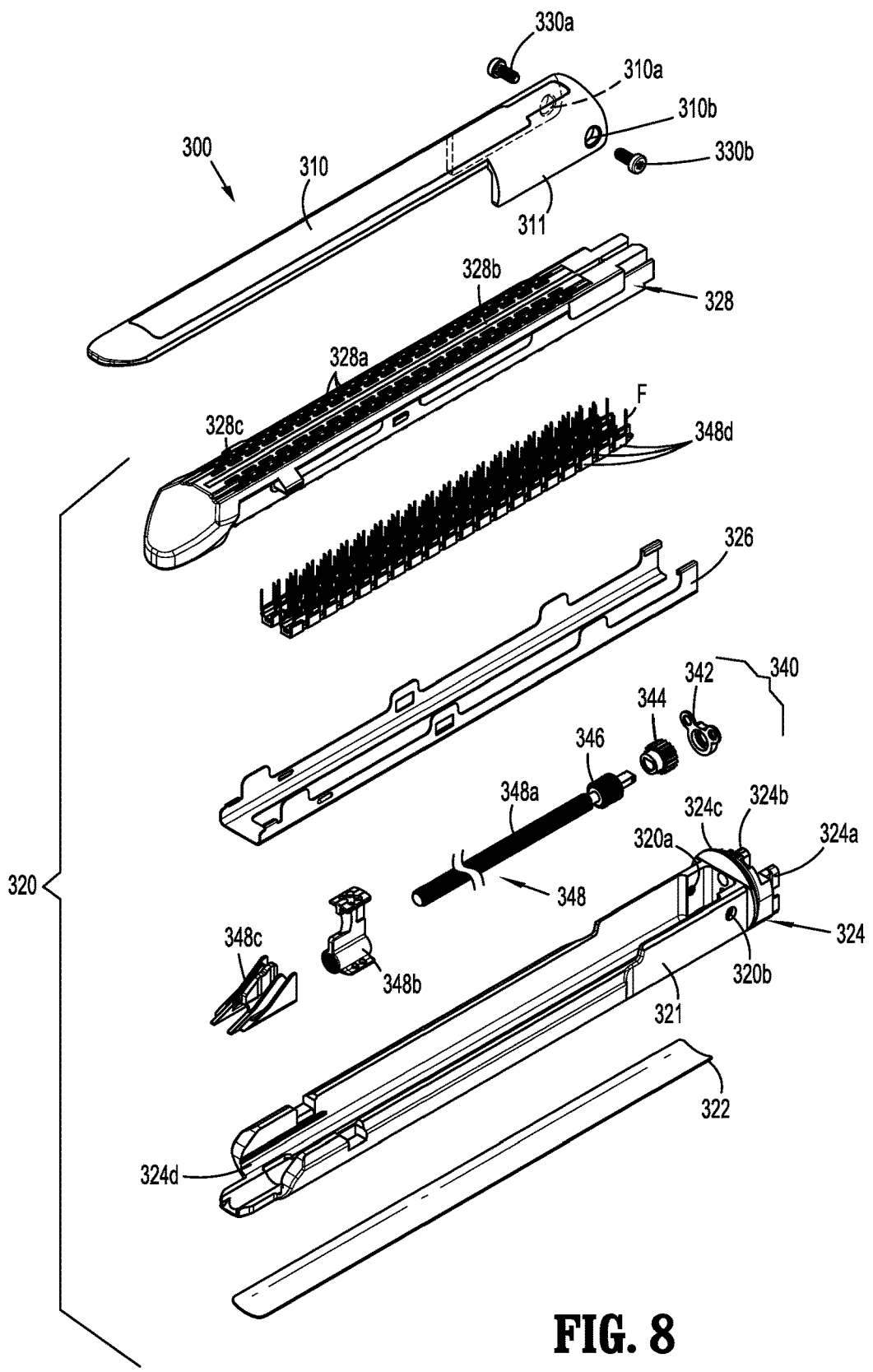
FIG. 8 is a perspective view, with parts separated, of the surgical loading unit of FIGS. 1, 6, and 7.

With reference now to FIGS. 3-5, in conjunction with FIGS. 1 and 2, adapter assembly 200 includes an adapter housing 202 at a proximal end portion thereof and an outer tube 204 that extends distally from adapter housing 202 to a distal end portion thereof. Adapter housing 202 and outer tube 204 are configured and dimensioned to house the components of the adapter assembly 200 therein. Outer tube 204 is dimensioned for endoscopic insertion, in particular, the outer tube 204 is passable through a typical trocar port, cannula, or the like. Adapter housing 202 is dimensioned so as to not enter the trocar port, cannula, or the like.

Adapter assembly 200 is configured to convert a rotation of one of rotatable drive connectors 108a, 108b, and 108c of surgical device 100 into axial translation useful for operating surgical loading unit 300. Adapter assembly 200 includes a surgical device drive coupling assembly 206 at a proximal end 200a thereof and an end effector coupling assembly 208 at a distal end 200b thereof. Surgical device drive coupling assembly 206 is configured and adapted to connect to the connecting portion 106 of handle housing 102 of surgical device 100. Surgical device drive coupling assembly 206 includes a drive coupling housing 206a dimensioned to be received within cylindrical recess 106a of connecting portion 106 of surgical device 100. Surgical device drive coupling assembly 206 rotatably supports first, second, and third connector sleeves 210a, 210b, and 210c. First connector sleeve 210a is configured to mate with first rotatable drive connector 108a of surgical device 100, second connector sleeve 210b is configured to mate with second rotatable drive connector 108b of surgical device 100, and third connector sleeve 210c is configured to mate with third rotatable drive connector 108c of surgical device 100.

Surgical device drive coupling assembly 206 rotatably supports a single rotatable drive shaft 212 that is configured and adapted to transmit/convert a speed/force of rotation of first rotatable drive connector 108a of surgical device 100 to loading unit 300. Rotatable drive shaft 212 includes a proximal end (not shown) operably connected with first connector sleeve 210a within drive coupling housing 206a and a distal end 212a disposed at distal end 200b of adapter assembly 200. Rotatable drive shaft 212 extends through a first fitting 214a disposed at a proximal end of outer tube 204 and a second fitting 214b disposed at a distal end of outer tube 204 to axially secure rotatable drive shaft 212 within adapter assembly 200. The rotatable drive shaft 212 functions as a rotation receiving member to receive rotational forces from first rotatable drive connector 108a of surgical device 100. A rotatable gear 216 (see FIG. 5), such as a spur gear, is disposed around distal end 212a of rotatable drive shaft 212 and configured to rotate therewith.

Referring now to FIGS. 6-11, loading unit 300 includes an anvil jaw 310 and a cartridge jaw 320 that are movable between open and closed positions with respect to each other. Anvil jaw 310 and cartridge jaw 320 are pinned together by a pair of pins 330a and 330b that are inserted through axially opposed openings 310a, 310b, and 320a, 302b in sidewalls 311 and 212 of anvil jaw 310 and cartridge jaw 320, respectively. Cartridge jaw 320 includes a base 322 secured to a mounting portion 324 having mating surfaces 324a, 324b on a proximal end 324c thereof. Mounting portion 324 defines a receiving channel 324d therein that supports a frame 326, a cartridge 328, and a fastener firing assembly 340 therein. Cartridge 328 defines a plurality of fastener retaining slots 328a and a knife slot 328b in a tissue engaging surface 328c thereof. A plurality of linear rows of fasteners "F", e.g., staples, are disposed within cartridge 328, with a single fastener "F" disposed in each fastener retaining slot 328a.

Fastener firing assembly 340 includes a proximal bearing member 342, a gear member 344 that engages gear 216 disposed around distal end 212a of drive shaft 212 at distal end 200*b* of adapter assembly 200, a distal bearing member 346, and a screw assembly 348. Screw assembly 348 includes a power screw 348*a* around which gear member 344 and distal bearing member 342 are disposed, a drive beam 348*b*, and an actuation sled 348*c* that is engagable with a plurality of pusher members 348*d* for ejecting the fasteners "F" from cartridge 328.

Cartridge jaw 320 includes a lock member 350 (FIG. 10), configured as a u- or c-shaped member, which is inserted through a sidewall 324*e* of mounting portion 324 and into distal bearing member 346 to secure power screw 348*a* axially within receiving channel 324*d* of cartridge jaw 320. Cartridge jaw 320 also includes a locking mechanism 360 (FIG. 11) disposed within a proximal portion of the mounting portion 324 for securing a proximal end 300*a* of surgical loading unit 300 with distal end 200*b* of adapter assembly 200. Locking mechanism 360 includes a frame 362 having a distal portion 362*a* including brackets 364*a* and 364*b* each defining a transverse slot 366*a* and 366*b* extending in a direction parallel to a longitudinal axis of cartridge jaw 320, a central portion 362*b* including a plate 368, and a proximal portion 362*c* including a rod 370 longitudinally extending proximally from central portion 362*b*. Slots 366*a* and 366*b* are axially aligned with opposed openings 320*a* and 320*b* of cartridge jaw 320 such that pins 330*a* and 330*b* extend through slots 366*a* and 366*b*. Slots 366*a* and 366*b* have an axially larger dimension than openings 320*a* and 320*b* to allow for longitudinal movement of the locking assembly 360 between an unlocked position and a locked position with respect to the adapter assembly 200.

Figure 11:
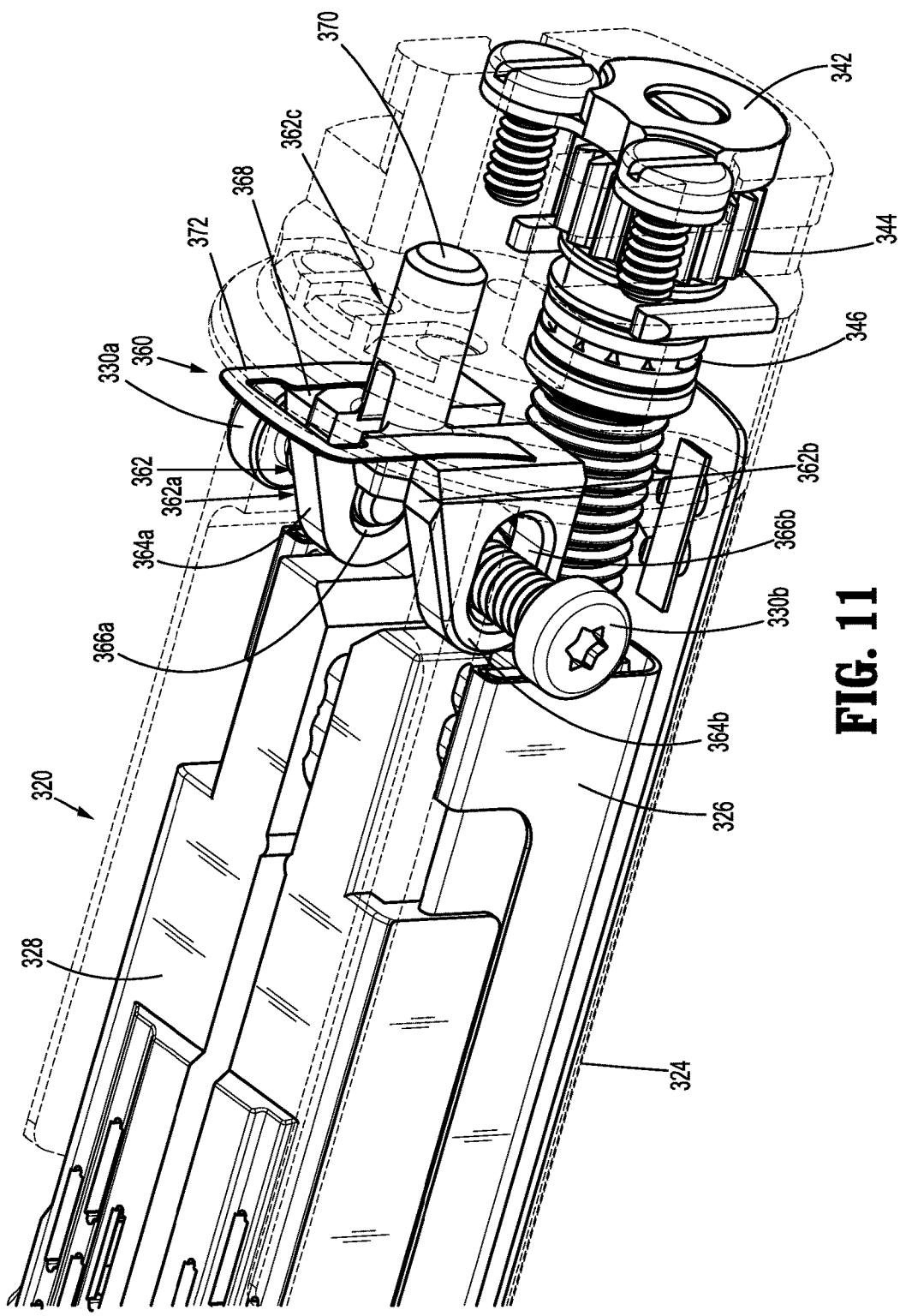
FIG. 11 is an enlarged top perspective view of a cartridge jaw of the surgical loading unit of FIGS. 1 and 6-10 with a mounting portion shown in phantom.

The locking mechanism 360 is biased to the unlocked position by spring 372 when cartridge 328 is free of, i.e., not loaded in, mounting portion 324 of cartridge jaw 320. Spring 372 biases locking mechanism 360 distally until proximal ends of slots 366*a* and 366*b* abut pins 330*a* and 330*b*. In the unlocked position, pins 330*a* and 330*b* are disposed in a proximal portion of slots 366*a* and 366*b* such that plate 368 is distally spaced from proximal end 324*c* of mounting portion 324 and rod 370 is recessed within, or distal to, a proximal opening 324*f* defined in proximal end 324*c* of mounting portion 324. When cartridge 328 is loaded into mounting portion 324, a proximal end of cartridge 328 cams against a distal end of locking mechanism 360 thereby moving locking mechanism 360 proximally such that plate 368 abuts proximal end 324*c* of mounting portion 324. In this position, pins 330*a* and 330*b* are positioned in a distal portion of slots 366*a* and 366*b*, and rod 370 extends through proximal opening 324*f* of proximal end 324*c* of mounting portion 324, as shown in FIG. 11.

Figure 12:
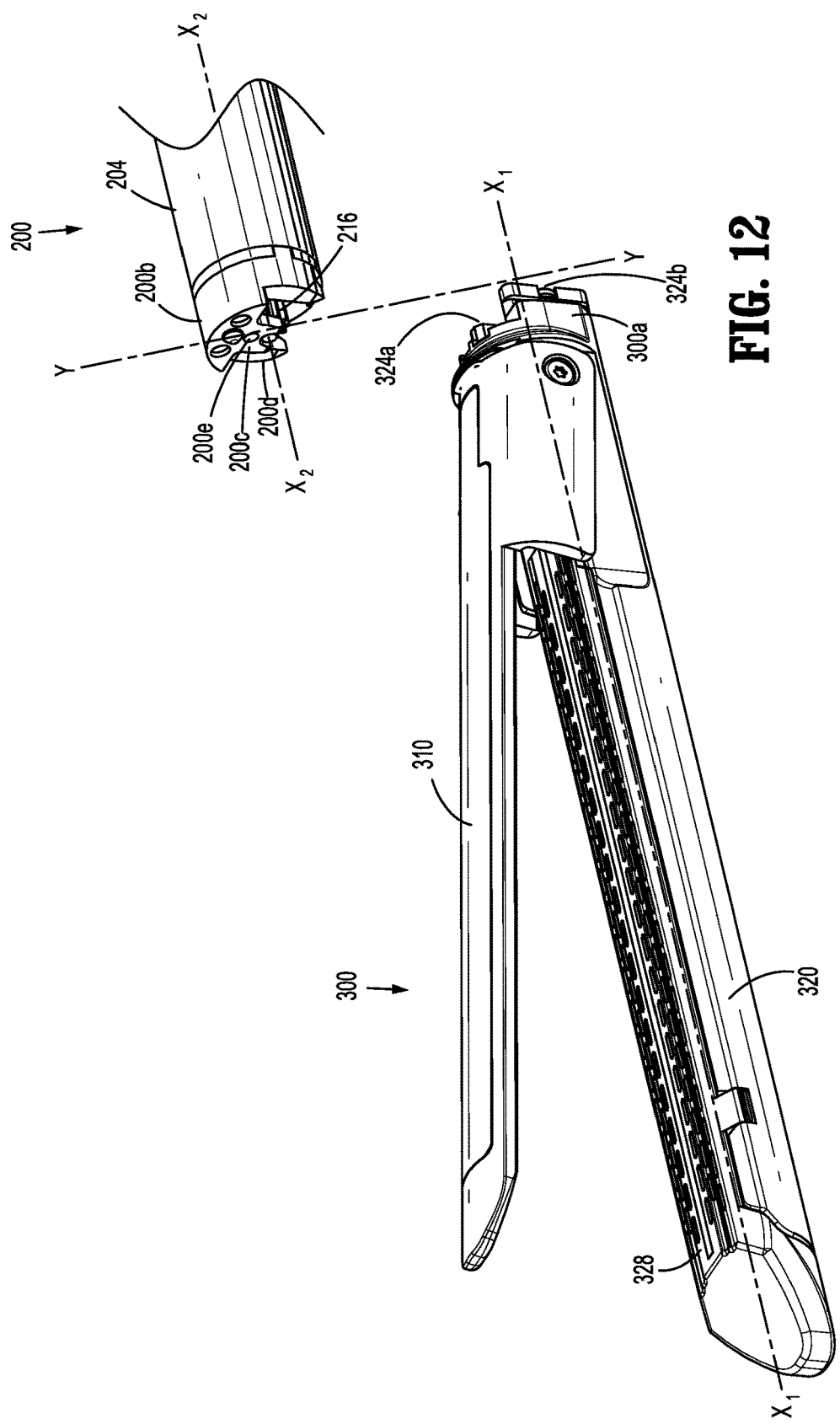
FIG. 12 is a perspective view illustrating an attachment of a proximal end of the surgical loading unit to a distal end of the adapter assembly of FIGS. 1-4.

In order to secure the proximal end 300*a* of surgical loading unit 300 to distal end 200*b* of adapter assembly 200, the cartridge jaw 320 must be free of a cartridge 328 so that the locking mechanism 360 is in the unlocked position. As shown in FIG. 12, surgical loading unit 300 and outer tube 204 of adapter assembly 200 are positioned along parallel longitudinal axes "X$_1$" and "X$_2$" with proximal end 300*a* of loading unit 300 aligned with distal end 200*b* of adapter assembly 200 along an axis "Y" transverse to axes "X$_1$" and "X$_2$". Proximal end 300*a* of loading unit 300 can be snapped together with distal end 200*b* of adapter assembly 200 by sliding at least one of surgical loading unit 300 and adapter assembly 200 along transverse axis "Y" so that surgical loading unit 300 and adapter assembly 200 are aligned along a common axis. In particular, mating surfaces 324*a*, 324*b* of loading unit 300 engage with mating surfaces 200*c* and 200*d* of adapter assembly 200 so that the teeth of gear member 344 of surgical loading unit 300 meshingly engage with the teeth of gear 216 of adapter assembly 200.

Thereafter, cartridge 328 is loaded into cartridge jaw 320 such that locking mechanism 360 is moved to the locked position. In the locked position, rod 370 of locking mechanism 360 is advanced through proximal opening 324*f* in proximal end 324*c* of mounting plate 324, past mating surface 324*a*, and into a recess 200*e* defined within mating surface 200*c* of adapter assembly 200 thereby locking or securing surgical loading unit 300 and adapter assembly 200 together. If the cartridge jaw 320 is preloaded with a cartridge 328, loading unit 300 cannot be properly coupled with adapter 200 as the rod 370 of locking mechanism 360 will block the coupling of adapter assembly 200 and loading unit 300.

In operation, actuation of one of the control buttons of surgical device 100 contacts one or more of a plurality of sensors (not shown) to electrically communicate with circuit board (not shown), to active first rotatable drive connector 108*a* (due to an actuation of a motor (not shown) within handle housing 102), and effectuate rotation of first drive connector 108*a*. Rotation of first drive connector 108*a* results in rotation of first connector sleeve 210*a* of adapter assembly 200, which causes rotation of drive shaft 212. Rotation of the drive shaft 212 causes rotation of gear 216 which in turn rotates gear member 344 of surgical loading unit 300. Rotation of gear member 344 rotates power screw 348*a* and enables drive beam 348*b* to axially advance along power screw 348*a* and through longitudinal knife slot 328*b* by virtue of the threaded engagement between power screw 348*a* and drive beam 348*b*. Drive beam 348*b* engages anvil jaw 310 to maintain anvil jaw 310 and cartridge jaw 320 in approximation. Distal advancement of drive beam 348*b* advances actuation sled 348*c* into engagement with the plurality of pusher members 348*d* and fires the plurality of fasteners "F" from the plurality of fastener retention slots 328*a* for forming against corresponding fastener forming pockets 312 defined within anvil jaw 310. Surgical loading unit 300 can be reset and cartridge 328 can be replaced so that surgical loading unit 300 can then be re-fired as desired.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An electromechanical surgical system, comprising:
   a hand held electromechanical surgical device including at least one rotatable drive connector supported in a handle housing;
   an adapter assembly selectively connectable to the surgical device, the adapter assembly including at least one rotatable drive sleeve configured to receive the at least one rotatable drive connector, a single rotatable drive shaft rotatably connected to the at least one rotatable drive sleeve and longitudinally extending to the distal end of the adapter assembly, and a gear disposed around a distal end of the rotatable drive shaft and configured to rotate with the rotatable drive shaft; and a surgical loading unit comprising an anvil jaw and a cartridge jaw that are operatively joined to one another such that the anvil jaw and the cartridge jaw are movable between open and closed positions relative to one another, the cartridge jaw including:

a mounting portion defining a receiving channel;

a power screw disposed within the receiving channel of the mounting portion;

a gear member mounted on a proximal portion of the power screw and operably engagable with the gear of the adapter assembly; and a locking mechanism disposed within the mounting portion for locking the surgical loading unit to the adapter assembly, the locking mechanism being movable between an unlocked position when the cartridge jaw is free of a cartridge and a locked position when a cartridge is loaded into the cartridge jaw.

2. The electromechanical surgical system of claim 1, wherein the locking mechanism is biased in the unlocked position by a spring.

3. The electromechanical surgical system of claim 1, wherein the locking mechanism includes a frame that is axially movable within a proximal portion of the mounting portion when a cartridge is loaded into and unloaded from the cartridge jaw.

4. The electromechanical surgical system of claim 3, wherein the frame includes a rod longitudinally extending proximally therefrom and dimensioned to extend through an opening in a proximal end of the mounting portion, wherein the rod extends proximally through the opening in the proximal end of the mounting portion when in the locked position and is recessed within or distal to the opening in the proximal end of the mounting portion when in the unlocked position.

5. The electromechanical surgical system of claim 4, wherein the rod extends into a recess in the distal end of the adapter assembly when in the locked position.

6. The electromechanical surgical system of claim 4, wherein the anvil jaw and the cartridge jaw are pinning together by a pair of pins extending through axially opposed openings in sidewalls of each of the anvil jaw and the cartridge jaw, and the frame includes a pair of transverse slots extending parallel to a longitudinal axis of the frame and aligned with the opposed openings in the sidewall of the cartridge jaw such that the pins extend through the opposed openings and into the slots, the slots having a larger axial dimension that the openings in the sidewall, wherein when the locking mechanism is in the locked position the pins are disposed within a distal portion of the slots and when the locking mechanism is in the unlocked position the pins are disposed in a proximal portion of the slots.

7. The electromechanical surgical system of claim 1, further comprising a lock member positioned through a sidewall of the mounting portion and into a distal bearing member to axially lock the power screw within the cartridge jaw.

* * * * *